United States Patent
Hwang et al.

(10) Patent No.: US 9,598,330 B2
(45) Date of Patent: Mar. 21, 2017

(54) PROCESS FOR REDUCING THE BENZENE CONTENT OF GASOLINE

(75) Inventors: Shyh-Yuan H. Hwang, Needham, MA (US); Ronald Birkhoff, Houston, TX (US); Richard F. Guarino, Fairhaven, MA (US); J. Erik Moy, South Grafton, MA (US); Geeta Pherwani, Watertown, MA (US)

(73) Assignee: BADGER LICENSING, Boston, MA (US)

(*) Notice: Subject to any disclaimer, the term of this patent is extended or adjusted under 35 U.S.C. 154(b) by 249 days.

(21) Appl. No.: 14/238,592

(22) PCT Filed: Nov. 30, 2011

(86) PCT No.: PCT/US2011/062635
§ 371 (c)(1),
(2), (4) Date: Feb. 12, 2014

(87) PCT Pub. No.: WO2013/028215
PCT Pub. Date: Feb. 28, 2013

(65) Prior Publication Data
US 2014/0194660 A1    Jul. 10, 2014

Related U.S. Application Data

(63) Continuation of application No. PCT/US2011/048463, filed on Aug. 19, 2011.

(51) Int. Cl.
*C07C 2/66* (2006.01)
*C07C 2/64* (2006.01)
*C10G 29/20* (2006.01)

(52) U.S. Cl.
CPC ............. *C07C 2/64* (2013.01); *C10G 29/205* (2013.01); *C07C 2529/70* (2013.01); *C10G 2300/1088* (2013.01); *C10G 2300/1092* (2013.01)

(58) Field of Classification Search
CPC ........................................................ C07C 2/66
USPC ................................................. 585/467, 449
See application file for complete search history.

(56) References Cited

U.S. PATENT DOCUMENTS

| | | | |
|---|---|---|---|
| 3,775,483 A | 11/1973 | Frederickson et al. | |
| 4,343,957 A | 8/1982 | Sartorio et al. | |
| 4,393,262 A | 7/1983 | Kaeding | |
| 4,891,458 A | 1/1990 | Innes et al. | |
| 4,950,823 A | 8/1990 | Harandi et al. | |
| 5,120,890 A * | 6/1992 | Sachtler | C10G 29/205 585/323 |
| 5,149,894 A | 9/1992 | Holtemrann et al. | |
| 5,491,270 A | 2/1996 | Chin et al. | |
| 5,545,788 A | 8/1996 | Cheng et al. | |
| 6,008,422 A | 12/1999 | Schulz et al. | |
| 6,835,862 B1 | 12/2004 | Gajda et al. | |
| 7,476,774 B2 | 1/2009 | Umansky et al. | |
| 2006/0194998 A1 * | 8/2006 | Umansky | C07C 2/66 585/467 |
| 2006/0194999 A1 | 8/2006 | Brown et al. | |
| 2008/0171900 A1 | 7/2008 | Schmidt | |
| 2010/0210886 A1 | 8/2010 | Brown et al. | |
| 2010/0249472 A1 | 9/2010 | Clark et al. | |
| 2010/0300930 A1 | 12/2010 | Clark et al. | |

FOREIGN PATENT DOCUMENTS

| | | |
|---|---|---|
| EP | 0485683 A1 | 11/1990 |
| WO | 2012108861 A1 | 8/2012 |
| WO | 2012108924 A1 | 8/2012 |
| WO | 2012108926 A1 | 8/2012 |

OTHER PUBLICATIONS

Laredo G C et al.: "Benzene reduction in gasoline by alkylation with olefins: Effect of the experimental conditions on 1 the product selectivity", Applied Catalysis A: General, Elsevier Science, Amsterdam, NL vol. 384, No. 1-2, Aug. 20, 2010, pp. 115-121.
Umansky B et al.: "Banish the benzene, boost the octane", Hydrocarbon Engineering, Palladian Publications, Farnham, GB, vol. 12, Jan. 1, 2007, pp. 61-62.
El-Mekki El Malki, Michael Clark: "BenzOUT Reducing Benzene Enhancing Gasoline Product Value", NPRA Conference, Phoenix, AZ, Mar. 21-23, 2010; XP00263231 1.
Pierre LePrince: "Le raffinage du petrole—3.Procédés de Transformation", Jan. 1, 1998, Technip, Paris, XP002670362, vol. 3.
The International Search Report and the Written Opinion of the International Searching Authority issued in the corresponding international application No. PCT/US2011/062635 on Feb. 14, 2012.
The International Search Report and the Written Opinion of the International Searching Authority issued in related international application No. PCT/US2011/023904 on May 20, 2011.
The International Search Report and the Written Opinion of the International Searching Authority issued in related international application No. PCT/US2011/062626 on Mar. 12, 2012.
The International Search Report and the Written Opinion of the International Searching Authority issued in related international application No. PCT/US2011/062648 on Mar. 16, 2012.

* cited by examiner

*Primary Examiner* — Thuan D Dang
(74) *Attorney, Agent, or Firm* — Roberts Mlotkowski Safran Cole & Calderon P.C.

(57) ABSTRACT

A process is described for alkylating benzene contained in a refinery gasoline stream, in which the refinery gasoline stream is contacted with an alkylating agent comprising one or more C2 to C5 olefins in an alkylation reaction zone under alkylation conditions to produce an alkylated effluent. The alkylation reaction zone comprises at least a first alkylation reaction stage and a second alkylation reaction stage and a portion of said alkylating agent is fed to each of said first and second alkylation reaction stages so that, although the molar ratio of alkylatable aromatic to alkylating agent in the total feed to the alkylation reaction zone is less than 1, the molar ratio of alkylatable aromatic to alkylating agent at the inlet of each of the first and second alkylation reaction stages is at least 1.0.

12 Claims, No Drawings

PROCESS FOR REDUCING THE BENZENE CONTENT OF GASOLINE

FIELD

This invention relates to a process for reducing the benzene content of gasoline.

BACKGROUND

Benzene is considered to be environmentally hazardous. As a result, the State of California and the United States Environmental Protection Agency have instituted regulations to limit the amount of benzene which may be present in gasoline. Beginning in January 2011, the US MSAT-2 (Mobile Source Air Toxics) regulation will require reduction of this annual average benzene content in gasoline to no greater than 0.62 volume %.

One known route for reducing the benzene content of gasoline is to selectively alkylate the benzene using a lower olefin. For example, Holtermann et al U.S. Pat. No. 5,149,894 describes a process for converting benzene to alkylated benzenes in a gasoline blend stock. The process involves contacting a benzene-containing gasoline blend stock with a C2 to C4 olefin stream in the presence of a catalyst containing the zeolite, SSZ-25, to produce an alkylated light hydrocarbon stream with reduced benzene content.

Cheng et al. U.S. Pat. No. 5,545,788 describes a process for the production of a more environmentally suitable gasoline by removing a substantial portion of benzene in gasoline by alkylation of reformate. The process involves alkylation using a light olefin feed at low temperature over the zeolite catalyst, MCM-49.

Umansky el al. U.S. Pat. No. 7,476,774 describes a process where light olefins including ethylene and propylene are extracted from refinery off-gases, such as from a catalytic cracking unit, into a light aromatic stream, such as a reformate containing benzene and other single ring aromatic compounds, which is then reacted with the light olefins to form a gasoline boiling range product containing alkylaromatics. The alkylation reaction is carried out in the liquid phase with a catalyst which preferably comprises a member of the MWW family of zeolites, such as MCM-22, using a fixed catalyst bed.

However, in addition to limiting the benzene level in gasoline, current and ongoing regulations restrict the content of residue, which consists of heavy hydrocarbon components with boiling points outside the gasoline boiling range. The US standard specification for automotive spark-ignition engine fuel (ASTM D4814) requires that the residue (heavies) in the gasoline product is no more than 2 volume %. As benzene regulations become more stringent, meeting the heavies level becomes an increasing problem because the light olefins used to alkylate the benzene in the gasoline can undergo undesirable competing reactions, such as olefin oligomerization to produce, for example, C6 to C8 olefins. Subsequent aromatic alkylation reactions result in the formation of heavies components, with boiling points outside of the typical gasoline boiling range.

According to the present invention, it has now been found that the undesirable formation of heavy components in the alkylation of a benzene-containing gasoline stream, such as a reformate or light naphtha, with an olefin alkylating agent can be reduced by conducting the alkylation reaction in at least two stages and splitting the olefin feed between the stages so that the molar ratio of alkylatable aromatic to alkylating agent in the feed to each stage is at least 1.0.

SUMMARY

In one aspect, the invention resides in a process for alkylating benzene contained in a refinery gasoline stream, said process comprising contacting said refinery gasoline stream with an alkylating agent comprising one or more C2 to C5 olefins in an alkylation reaction zone under alkylation conditions to produce an alkylated effluent, wherein said alkylation reaction zone comprises at least a first alkylation reaction stage and a second alkylation reaction stage, wherein a portion of said alkylating agent is fed to each of said first and second alkylation reaction stages so that, although the molar ratio of alkylatable aromatic to alkylating agent in the total feed to the alkylation reaction zone is less than 1, the molar ratio of alkylatable aromatic to alkylating agent at the inlet of each of said first and second alkylation reaction stages is at least 1.0, for example, from about 1.0 to about 2.0.

The alkylated effluent from the alkylation reaction zone may be removed from the alkylation reaction zone without recycle to either of the first and second alkylation reaction stages.

The refinery gasoline stream may be, for example, a reformate or a light naphtha. The alkylating agent may be, for example, propylene.

The refinery gasoline stream may comprise at least 10 wt % benzene. The effluent from the reaction zone may comprise less than 1 volume % benzene, for example, less than 0.62 volume % benzene.

The alkylated effluent from the reaction zone may comprise no more than 2 volume % of compounds having a boiling point greater than the boiling point of 1,3,5-trisisopropylbenzene.

The alkylation reaction in each of said first and second alkylation reaction stages may take place over a catalyst comprising an MWW zeolite.

The refinery gasoline stream may be substantially in the liquid phase during contact with the alkylating agent in the alkylation reaction zone.

DETAILED DESCRIPTION

Refinery streams which may be alkylated to decrease benzene content include streams comprising benzene and alkylbenzenes. Examples of such streams include reformates and naphtha streams, especially light naphtha streams (typically boiling in the range from about 40° C. to about 150° C.). Blends of refinery streams may also be alkylated.

Reformates have high octane number attributable to their high aromatics content. However, high concentrations of benzene in reformate, e.g., 4 to 6 wt %, can limit reformate utility as a blending component where environmental considerations require low benzene levels in gasoline product (no greater than 1 vol %). Various efforts to reduce benzene content in reformate, e.g., selective hydrogenation, high temperature fluid-bed MBR, and reformate alkylation with methanol all suffer from octane losses or total liquid product losses associated with undesired cracking of C5+ non-aromatics.

The present invention relates to a process whereby benzene-containing reformates and other refinery streams are treated to reduce benzene content by alkylation. Undesirable alkylation of higher boiling aromatics, such as xylenes, may be minimized.

The catalyst employed in the present invention, may comprise an MWW member family zeolite. Zeolites of the MWW family are described in U.S. Pat. No. 7,476,774.

Examples of suitable alkylating agents for use in the present invention are olefins such as ethylene, propylene, the butenes, and the pentenes. Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, and FCC off-gas, etc., are useful alkylating agents herein. Compositions of examples of olefin containing streams suitable for use as alkylating agents are described, for example, in U.S. Pat. No. 7,476,774.

The alkylation process is conducted such that the organic reactants, i.e., the alkylatable aromatic compound and the alkylating agent, are brought into contact with a zeolite catalyst composition in a suitable reaction zone comprising at least a first alkylation reaction stage and a second alkylation reaction stage connected in series. For example, the alkylation process may be conducted in a flow reactor containing first and second fixed beds of the catalyst composition. An equal portion of the alkylating agent is fed to each reaction stage, while all of the gasoline feed is supplied to the first alkylation stage. In this way, although the molar ratio of alkylatable aromatic to alkylating agent in the total feed to the process is less than 1, the molar ratio of alkylatable aromatic to alkylating agent at the inlet of each of the first and second alkylation reaction stages is at least 1.0, such as from 1 to 2.

The alkylation process is typically conducted under conditions including a temperature of from about 0° C. to about 500° C., for example, between about 50° C. and about 250° C., a pressure of from about 0.2 to about 250 atmospheres, for example, from about 1 to about 25 atmospheres, a feed weight hourly space velocity (WHSV) of between 0.1 $hr^{-1}$ and 500 $hr^{-1}$, for example, from 0.5 $hr^{-1}$ to 100 $hr^{-1}$. The latter WHSV is based upon the total weight of active catalyst (and binder if present).

The reactants may be in the vapor phase or the liquid phase or in a mixture of liquid and vapor phases. The reactants may be neat, i.e., free from intentional admixture or dilution with other material, or they can be brought into contact with the zeolite catalyst composition with the aid of carrier gases or diluents such as, for example, hydrogen or nitrogen.

Catalyst System

The catalyst system used in the alkylation of the present process is preferably one based on a zeolite of the MWW family because these catalysts exhibit excellent activity for the desired aromatic alkylation reaction using light olefins, especially propylene. It is, however, possible to use other molecular sieve catalysts for this alkylation, including catalysts based on ZSM-12 as described in U.S. Pat. Nos. 3,755,483 and 4,393,262 for the manufacture of petrochemical cumene from refinery benzene and propylene or catalysts based on zeolite beta as described in U.S. Pat. No. 4,891,458, all of which are reported to have activity for the alkylation of light aromatics by propylene.

MWW Zeolite

The MWW family of zeolite materials has achieved recognition as having a characteristic framework structure which presents unique and interesting catalytic properties. The MWW topology consists of two independent pore systems: a sinusoidal ten-member ring [10 MR] two dimensional channel separated from each other by a second, two dimensional pore system comprised of 12 MR super cages connected to each other through 10 MR windows. The crystal system of the MWW framework is hexagonal and the molecules diffuse along the [100] directions in the zeolite, i.e., there is no communication along the c direction between the pores. In the hexagonal plate-like crystals of the MWW type zeolites, the crystals are formed of relatively small number of units along the c direction as a result of which, much of the catalytic activity is due to active sites located on the external surface of the crystals in the form of the cup-shaped cavities. In the interior structure of certain members of the family such as MCM-22, the cup-shaped cavities combine together to form a supercage. The MCM-22 family of zeolites has attracted significant scientific attention since its initial announcement by Leonovicz et al. in Science 264, 1910-1913 [1994] and the later recognition that the family includes a number of zeolitic materials such as PSH 3, MCM-22, MCM-49, MCM-56, SSZ-25, ERB-1, ITQ-1, and others. Lobo et al. AlChE Annual Meeting 1999, Paper 292J.

The relationship between the various members of the MCM-22 family have been described in a number of publications. Significant members of the family are MCM-22, MCM-36, MCM-49, and MCM-56. When initially synthesized from a mixture including sources of silica, alumina, sodium, and hexamethylene imine as an organic template, the initial product will be MCM-22 precursor or MCM-56, depending upon the silica:alumina ratio of the initial synthesis mixture. At silica:alumina ratios greater than 20, MCM-22 precursor comprising H-bonded vertically aligned layers is produced whereas randomly oriented, non-bonded layers of MCM-56 are produced at lower silica:alumina ratios. Both these materials may be converted to a swollen material by the use of a pillaring agent and on calcination, this leads to the laminar, pillared structure of MCM-36. The as-synthesized MCM-22 precursor can be converted directly by calcination to MCM-22 which is identical to calcined MCM-49, an intermediate product obtained by the crystallization of the randomly oriented, as-synthesized MCM-56. In MCM-49, the layers are covalently bonded with an interlaminar spacing slightly greater than that found in the calcined MCM-22/MCM-49 materials. The as-synthesized MCM-56 may be calcined itself to form calcined MCM-56 which is distinct from calcined MCM-22/MCM-49 in having a randomly oriented rather than a laminar structure. In the patent literature MCM-22 is described in U.S. Pat. No. 4,954,325 as well as in U.S. Pat. Nos. 5,250,777; 5,284,643 and 5,382,742. MCM-49 is described in U.S. Pat. No. 5,236,575; MCM-36 in U.S. Pat. No. 5,229,341 and MCM-56 in U.S. Pat. No. 5,362,697.

A preferred zeolitic material for use as the MWW component of the catalyst system is MCM-22. It has been found that the MCM-22 may be either used fresh, that is, not having been previously used as a catalyst or, alternatively, regenerated MCM-22 may be used. Regenerated MCM-22 may be used after it has been used in any of the catalytic processes for which it is known to be suitable but one form of regenerated MCM-22 which has been found to be highly effective in the present condensation process is MCM-22 which has previously been used for the production of aromatics such as ethylbenzene or cumene, normally using reactions such as alkyaltion and transalkylation. The cumene production (alkylation) process is described in U.S. Pat. No. 4,992,606 (Kushnerick et al). Ethylbenzene production processes are described in U.S. Pat. No. 3,751,504 (Keown); U.S. Pat. No. 4,547,605 (Kresge); and U.S. Pat. No. 4,016, 218 (Haag); U.S. Pat. Nos. 4,962,256; 4,992,606; 4,954,663; 5,001,295; and 5,043,501 describe alkylation of aromatic compounds with various alkylating agents over catalysts comprising MWW zeolites such as PSH-3 or MCM-22. U.S. Pat. No. 5,334,795 describes the liquid phase synthesis of ethylbenzene with MCM-22.

The MCM-22 catalysts may be regenerated after catalytic use in aromatics production processes by conventional air oxidation techniques similar to those used with other zeolite catalysts.

Catalyst Matrix

In addition to the zeolitic component, the catalyst will usually contain a matrix material or binder in order to give adequate strength to the catalyst as well as to provide the desired porosity characteristics in the catalyst. High activity catalysts may, however, be formulated in the binder-free form by the use of suitable extrusion techniques, for example, as described in U.S. Pat. No. 4,908,120. When used, matrix materials suitably include alumina, silica, silica alumina, titania, zirconia, and other inorganic oxide materials commonly used in the formulation of molecular sieve catalysts. For use in the present process, the level of zeolite, such as MCM-22 or ZSM-5 type (intermediate pore size) zeolite, in the finished matrixed catalyst will be typically from 20 to 70% by weight, and in most cases from 25 to 65% by weight. In manufacture of a matrixed catalyst, the active ingredient will typically be mulled with the matrix material using an aqueous suspension of the catalyst and matrix, after which the active component and the matrix are extruded into the desired shape, for example, cylinders, hollow cylinders, trilobe, quadlobe, etc. A binder material such as clay may be added during the mulling in order to facilitate extrusion, increase the strength of the final catalytic material and to confer other desirable solid state properties. The amount of clay will not normally exceed 10% by weight of the total finished catalyst. Unbound (or, alternatively, self-bound) catalysts are suitably produced by the extrusion method described in U.S. Pat. No. 4,582,815, to which reference is made for a description of the method and of the extruded products obtained by its use. The method described there enables extrudates having high constraining strength to be produced on conventional extrusion equipment and accordingly, the method is suitable for producing the catalysts which are silica-rich. The catalysts are produced by mulling the zeolite with water to a solids level of 25 to 75 wt % in the presence of 0.25 to 10 wt % of basic material such as sodium hydroxide. Further details are to be found in U.S. Pat. No. 4,582,815.

Comparative Example 1

Alkylation of a synthetic benzene containing reformate stream with propylene was carried out in a fixed bed once-through reactor. The reactor was loaded with a fixed bed alkylation catalyst. The synthetic reformate feed comprised 15% benzene, 4% toluene and 81% n-heptane and was introduced into the reactor at a flow rate of 100 grams per hour, and the reactor was heated up to the reaction temperature of 200° C. before propylene charge was introduced. The reactor pressure was kept above the vapor pressure of the reaction mixture to ensure liquid phase operation. The reactor performance was evaluated at three different propylene charge rates. The results are listed in Table 1, wherein the charge rates are designated as 1A, 1B and 1C.

TABLE 1

| Case | 1A | 1B | 1C |
|---|---|---|---|
| Feed Aromatic to Propylene Ratio (molar) | 0.92 | 0.80 | 0.65 |
| Aromatic to Propylene Ratio at Reactor Inlet (molar) | 0.92 | 0.80 | 0.65 |
| Effluent Benzene (volume %) | 2.3 | 1.6 | 0.70 |
| Effluent Heavies (volume %) | 0.8 | 1.3 | 2.9 |
| Benzene Conversion (%) | 82 | 87 | 94 |

As shown in Table 1, the benzene content in the reactor effluent decreased as propylene charge was increased. However, the effluent heavies content also increased with increasing propylene charge and went above 2 volume % before the target 0.62 volume % benzene content was reached. The heavies content includes all the compounds that have a higher boiling point than 1,3,5-trisisopropylbenzene. This reactor system was therefore not capable of achieving both high benzene conversion and low heavies make simultaneously and was unable to produce a gasoline product that met both the <0.62 volume % benzene content and the <2 volume % distillation residue specifications without fractionation of the reactor effluent to remove excess benzene and/or heavies.

Example 2

A second reactor was connected in series to and downstream of the first reactor of Comparative Example 1. The reformate feed was fed to the first reactor with a first portion of the same propylene charge. The effluent from the first reactor was fed to the second reactor together with a second equal portion of propylene charge. The same synthetic reformate feed described in Comparative Example 1 was introduced into the first reactor at a flow rate of 100 grams per hour, and the reactors were heated up to the reaction temperature of 200° C. before propylene charge was introduced. The reactor pressure was kept above the vapor pressure of the reaction mixture to ensure liquid phase operation. The reactor performance was evaluated at three different propylene charge rates, and the propylene charge was equally distributed between the two reactors. The results are listed in Table 2, wherein the charge rates are designated as 2A, 2B and 2C.

TABLE 2

| Charge Rate | 2A | 2B | 2C |
|---|---|---|---|
| Feed Aromatic to Propylene Ratio (molar) | 0.80 | 0.70 | 0.66 |
| Aromatic to Propylene Ratio at each Reactor Inlet (molar) | 1.6 | 1.4 | 1.3 |
| Effluent Benzene (volume %) | 1.4 | 0.82 | 0.59 |
| Effluent Heavies (volume %) | 0.8 | 1.3 | 1.7 |
| Benzene Conversion (%) | 89 | 93 | 95 |

Since the synthetic reformate feed went through both reactors while the propylene feed was evenly distributed between the two reactors and completely consumed in the first reactor, the aromatic to propylene ratio at the inlet of each of the two reactors was twice of that in the overall feeds. As shown in Table 2, the benzene content in the reactor effluent decreased and the heavies content increased as the propylene charge was increased, in a way similar to that shown in the Comparative Example. The benzene content in this example, however, reached the desired <0.62 volume % level before the heavies content exceeded the 2 volume % limit. The two-reactor system employed in this Example was therefore shown capable of achieving both high benzene conversion and low heavies make simultaneously and produced a gasoline product that met both the <0.62 volume % benzene content and <2 volume % distillation residue specifications without fractionation of the reactor effluent to remove excess benzene and/or heavies. By comparing the results from Comparative Example 1 and this Example 2, the reactor inlet aromatic to propylene (A/P) molar ratio is found to be a major factor that affects the production of heavies. As the A/P ratio is lowered, more and more propylene oligomerizes and cracks. In the meantime, these oligomers react with benzene and alkylated benzenes to form heavies. By controlling the reactor inlet aromatic to propylene ratio, one can then control the propylene oligomerization reaction and heavies make.

What is claimed is:

1. A process for alkylating benzene contained in a refinery gasoline stream, said process comprising contacting said refinery gasoline stream with an alkylating agent comprising one or more C2 to C5 olefins in an alkylation reaction zone under alkylation conditions to produce an alkylated effluent, wherein said alkylation reaction zone consists of a first alkylation reaction stage and a second alkylation reaction stage, wherein a portion of said alkylating agent is fed to each of said first and second alkylation reaction stages so that the molar ratio of alkylatable aromatic to alkylating agent in the total feed to the alkylation reaction zone is less than 1, and the molar ratio of alkylatable aromatic to alkylating agent at the inlet of each of said first and second alkylation reaction stages is at least 1.0, wherein the alkylation reaction in each of said first and second alkylation reaction stages takes place over a catalyst comprising an MWW zeolite.

2. A process according to claim 1, wherein the molar ratio of alkylatable aromatic to alkylating agent at the inlet of each of said first and second alkylation reaction stages is from 1.0 to about 2.0.

3. A process according to claim 1, wherein said alkylated effluent is removed from said alkylation reaction zone without recycle to either of said first and second alkylation reaction stages.

4. A process according to claim 1, wherein said refinery gasoline stream is a reformate or a light naphtha.

5. A process according to claim 1, wherein said alkylating agent is propylene.

6. A process according to claim 1, wherein said refinery gasoline stream comprises at least 10 wt % benzene.

7. A process according to claim 1, wherein said alkylated effluent comprises less than 1 volume % benzene.

8. A process according to claim 1, wherein said alkylated effluent comprises less than 0.62 volume % benzene.

9. A process according to claim 1, wherein said alkylated effluent comprises no more than 2 volume % of compounds having a boiling point greater than the boiling point of 1,3,5-trisisopropylbenzene.

10. A process according to claim 1, wherein said refinery gasoline stream is substantially in the liquid phase during said contacting.

11. A process according to claim 8, wherein the alkylated effluent comprises less than 2 volume % distillation residue without fractionation of the reactor effluent to remove excess benzene and/or heavies.

12. A process according to claim 1, wherein the molar ratio of alkylatable aromatic to alkylating agent in the total feed to the alkylation reaction zone is between 0.5 and 1.

* * * * *

UNITED STATES PATENT AND TRADEMARK OFFICE
CERTIFICATE OF CORRECTION

PATENT NO. : 9,598,330 B2
APPLICATION NO. : 14/238592
DATED : March 21, 2017
INVENTOR(S) : Shyh-Yuan H. Hwang et al.

Page 1 of 1

It is certified that error appears in the above-identified patent and that said Letters Patent is hereby corrected as shown below:

On the Title Page

Item (73) should read:
Assignee: BADGER LICENSING LLC, Boston, MA (US)

Signed and Sealed this
Fourth Day of July, 2017

Joseph Matal
*Performing the Functions and Duties of the*
*Under Secretary of Commerce for Intellectual Property and*
*Director of the United States Patent and Trademark Office*